[12] United States Patent
Guan et al.

(10) Patent No.: US 9,892,503 B2
(45) Date of Patent: Feb. 13, 2018

(54) MONITORING CHANGES IN PHOTOMASK DEFECTIVITY (71) Applicant: KLA-Tencor Corporation, Milpitas, CA (US)

(72) Inventors: Chun Guan, Dublin, CA (US); Yalin Xiong, Pleasanton, CA (US); Joseph M. Blecher, San Jose, CA (US); Robert A. Comstock, Pleasanton, CA (US); Mark J. Wihl, Tracy, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/344,788

(22) Filed: Nov. 7, 2016

(65) Prior Publication Data
US 2017/0053395 A1 Feb. 23, 2017

Related U.S. Application Data (63) Continuation of application No. 14/278,277, filed on May 15, 2014, now Pat. No. 9,518,935.
(Continued)

(51) Int. Cl.
*G01N 21/00* (2006.01)
*G06T 7/00* (2017.01)
*G01N 21/956* (2006.01)

(52) U.S. Cl.
CPC ......... *G06T 7/0006* (2013.01); *G01N 21/956* (2013.01); *G01N 21/95607* (2013.01);
(Continued)

(58) Field of Classification Search
CPC ... G01N 2021/95676; G01N 21/95607; G01N 21/956; F02M 25/00; F16L 11/10; G06T 2207/30148; G06T 7/0006
(Continued)

(56) References Cited

U.S. PATENT DOCUMENTS 6,614,520 B1 9/2003 Bareket et al.
7,873,204 B2 1/2011 Wihl et al.
(Continued)

FOREIGN PATENT DOCUMENTS

CN 102084396 A 6/2011
CN 102792297 A 11/2012
JP 2010-262506 A 11/2010

OTHER PUBLICATIONS

"U.S. Appl. No. 14/278,277, Non Final Office Action dated Feb. 16, 2016", 5 pages.
(Continued)

*Primary Examiner* — Tri T Ton
(74) *Attorney, Agent, or Firm* — Kwan & Olynick, LLP (57) ABSTRACT A reticle that is within specifications is inspected to generate baseline candidate defects and their location and size. After using the reticle in photolithography, the reticle is inspected to generate current candidate defects and their location and size. An inspection report of filtered candidate defects and their images is generated so that these candidate defects include a first subset of the current candidate defects and their images and exclude a second subset of the current candidate defects and their images. Each of the first subset of candidate defects has a location and size that fails to match any baseline candidate defect's location and size, and each of the excluded second subset of candidate defects has a location and size that matches a baseline candidate defect's location and size.

28 Claims, 6 Drawing Sheets

Related U.S. Application Data (60) Provisional application No. 61/859,670, filed on Jul. 29, 2013.

(52) U.S. Cl.
CPC .............. *G01N 2021/95676* (2013.01); *G06T 2207/30148* (2013.01)

(58) Field of Classification Search
USPC ...................... 356/237.1–237.4, 239.1–239.8
See application file for complete search history.

(56) References Cited

U.S. PATENT DOCUMENTS

| | | |
|---|---|---|
| 9,518,935 B2 | 12/2016 | Guan et al. |
| 2003/0091224 A1 | 5/2003 | Wiley et al. |
| 2008/0304056 A1 | 12/2008 | Alles et al. |
| 2011/0286658 A1 | 11/2011 | Mitsui |
| 2012/0331487 A1 | 12/2012 | Mikami |
| 2015/0029498 A1 | 1/2015 | Guan et al. |

OTHER PUBLICATIONS

"U.S. Appl. No. 14/278,277, Notice of Allowance dated Jun. 22, 2016", 7 pages.
"U.S. Appl. No. 14/278,277, Notice of Allowance dated Oct. 6, 2016", 7 pages.
"Int'l Application Serial No. PCT/US2014/048720, Search Report and Written Opinion dated Nov. 12, 2014", 10 pages.
"Chinese Application Serial No. 201480049582.0, Office Action dated Apr. 12, 2017", 9 pgs.

MONITORING CHANGES IN PHOTOMASK DEFECTIVITY

CROSS-REFERENCE TO RELATED APPLICATIONS

This application is a continuation of and claims the benefit under 35 U.S.C. § 120 of U.S. application Ser. No. 14/278,277, filed 15 May 2014, entitled "Monitoring Changes in Photomask Defectivity" by Chun Guan et al., which claims priority under 35 U.S.C. § 119 of prior U.S. Provisional Application No. 61/859,670, filed Jul. 29, 2013, titled "Methods for Monitoring Changes in Photomask Defectivity" by Chun Guan et al. These applications are herein incorporated by reference in their entireties for all purposes.

TECHNICAL FIELD OF THE INVENTION

The invention generally relates to the field of reticle inspection. More particularly the present invention relates to techniques for requalifying single-die reticles in the IC (integrated circuit) fabrication context.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device is fault free prior to shipment to the end users or customers.

An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write (e.g., typically, an electron beam writer or laser scanner is used to expose a reticle pattern) a plurality of reticles that will later be used to fabricate the particular IC design. A reticle inspection system may then inspect the reticle for defects that may have occurred during the production of the reticles.

A reticle or photomask is an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication processes.

After fabrication of each reticle or group of reticles, each new reticle typically is free of defects or degradation. However, the reticle may become defective after use. Thus, there is a continuing need for improved reticle inspection techniques, especially single-die reticles.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting a photolithographic reticle is disclosed. An reticle inspection tool is used to perform a first single-die inspection of a reticle that is has been identified as being within specifications so as to generate a plurality of baseline events corresponding to a plurality of unusual baseline features of the reticle, and each baseline event indicates a location and size value for a corresponding unusual baseline feature. Alternatively, the baseline events are generated based on an image of the reticle that is simulated from a design database of the reticle. Periodically, after every so many exposures using the reticle, the reticle is requalified by performing a subsequent inspection. Each subsequent inspection generates a plurality of current events corresponding to a plurality of current unusual features on the reticle, and each current event indicates a location and a size value for a corresponding current unusual feature.

During the subsequent inspections, any current unusual event that matches a baseline event within a prescribed location and size tolerance is deemed an uninteresting or false defect and is discarded. Only the current unusual events for which there are no baseline event matches are kept for further processing. Those events that survive all processing steps are considered reviewable defects. Reviewable defects are reported with sufficient information to allow them to be properly dispositioned. By discarding false and uninteresting events early on: the user is spared reviewing them, some processing time and expense is saved, and the data volume of the inspection report is minimized.

In certain embodiments, matches between the current unusual events and baseline current events are found by first finding reference images for a subset of the unusual events and their corresponding test images. Candidate defects are found based on a comparison between each reference and test image. One or more current candidate defects are found for each unusual event that has a reference image, and it can be determined whether a location and size of each one or more current candidate defects can be matched to a baseline location and size of a baseline candidate defect.

In either embodiment, the inspection driven baseline or the database driven baseline, the baseline generation can be augmented to also save pattern data for all sections of the pattern for which suitable references cannot be found or synthesized at run time. In this way subsequent inspections can use the pattern data saved in the baseline to augment the found and synthesized references so that all patterns may have references. This baseline can allow 100% coverage using comparison techniques during all subsequent single die inspections.

In a specific embodiment, an inspection report of a plurality of candidate reticle defects and their images is generated so that the candidate defects include a first subset of the current events and their corresponding plurality of candidate defect images and exclude a second subset of the current events and their corresponding plurality of excluded images. Each of the first subset of events included in the inspection report has a location and size value that fails to match any baseline event's location and size value by a predefined amount, and each of the second subset of events excluded from the inspection report has a location and size value that matches any baseline event's location and size value by the predefined amount.

In one aspect, at least some of the baseline events correspond to a plurality of reticle features that were designed to be identical prior to an optical proximity correction (OPC) process being implemented on such reticle features to add OPC decorations so that such reticle features are no longer identical. In another aspect, at least some of the baseline events correspond to reticle features that were not part of an original design for such reticle and were determined to not limit wafer yield using such reticle. In yet another aspect, at least some of the baseline events correspond to reticle features that have been determined to not print onto a wafer during a photolithography process using the reticle. In another aspect, at least some of the baseline events correspond to repair features for correcting defects on the reticle.

In one example, the first and second single-die inspections determine which features of the reticle are atypical based on the context of such features. In a further aspect, the first and second single-die inspections include template matching. In one implementation, the method includes discarding a plurality of baseline images for the baseline events and discarding the second subset of candidate events' corresponding images. In another example, each baseline event further indicates a channel and each of the second subset of events excluded from the inspection report has a channel and a location and size value that matches any baseline event's channel and location and size value by a predefined amount.

In an alternative embodiment, generating the inspection report of the candidate defects and their images comprises, for each current event that has a location and size value that fails to match any baseline event's location and size value by a predefined amount, determining whether such current event is a candidate defect by performing a third single-die inspection that has a less stringent threshold or algorithm than the second single-die inspection. In another aspect, the candidate defect images and the excluded images include one or more combinations of reflected images, transmitted images, or combined reflected and transmitted images. In one instance, the candidate defects further include a third subset of current events that each has a location and size value that matches any baseline event's location and size value by a predefined amount and is identified as a repair location.

In certain embodiments, the invention pertains to a system for inspecting a photolithographic reticle. The system includes at least one memory and at least one processor that are configured to perform at least some of the above described operations. In other embodiments, the invention pertains to computer readable media having instructions stored thereon for performing at least some of the above described operations.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Single-die reticles present particular inspection challenges for the fab requal use case. Multi-die reticles can be inspected using techniques that compare the images acquired from one die to images acquired from of a second die. Alternatively, both single-die and multi-die reticles can be inspected using techniques that compare the images acquired from the reticle to images rendered from the post-OPC (optical proximity correction) database. This second technique requires access to the post-OPC database and is typically deemed too costly and/or too complex to be practical for fabrication requalification of a reticle. After all, the pattern fidelity of the reticle has already been verified by mask shop or incoming quality control inspections. Requalification inspections need only find defects that get added during reticle usage. However, without a second die- or a database-provided reference, finding these defects on a single-die reticle can be challenging.

Certain non-comparison techniques can be used to find defects whose signatures are never expected to appear on non-defective reticles. However, even for single die reticles, some comparison techniques can still be used to find most of the defects of interest. When sections of the patterns are repeated or are simple enough to be self-referencing, reference patterns can be found or synthesized. Comparisons to these found or synthesized references can be used to detect defects. There are two main deficiencies when using such comparison techniques for the inspection of single-die reticles. First, there is the problem of coverage. Suitable references cannot be found or synthesized for all sections of the pattern. Second, there is a problem with false detections. Some detections may be triggered by unusual but deliberate variations in the pattern. These are most often due to OPC variations.

Figure 1A:
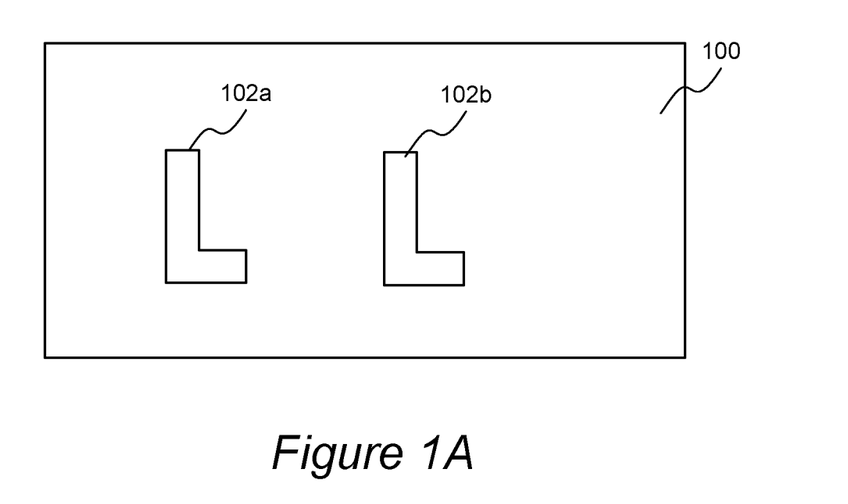
FIG. 1A is a diagrammatic top view of a reticle portion having two pre-OPC features that have a same shape and size.

A photolithograhy mask or reticle can include device design data that is generated by circuit and layout designers and/or synthesis tools. Pre-OPC design data generally include polygons that were generated by a designer or synthesis tool for a particular reticle prior to any OPC structures being added to the design data. The pre-OPC design data can be said to represent the intention of the designer and will generally resemble the final wafer, which will be fabricated with a reticle that is made using the reticle design data. FIG. 1A is a diagrammatic top view of a reticle portion 100 having two pre-OPC features 102a and 102b that have a same shape and size.

The reticle design data may include OPC decorations that are added to the pre-OPC reticle design data. In general, OPC software is used to analyze a reticle design and then add OPC decorations to a reticle design based on such analysis. The OPC decorations enhance the fabrication of the reticle. For example, a sharper image may be obtained on corners if certain OPC enhancements are added proximate to such corners in the design data.

One or more OPC-generating models may be applied to the pre-OPC design so that OPC structures are generated based on such models. The models may be based on experimental and/or simulation results. In general, the terms OPC, SRAF, thin-line, and non-printable structures are used interchangeably herein.

Figure 1B:
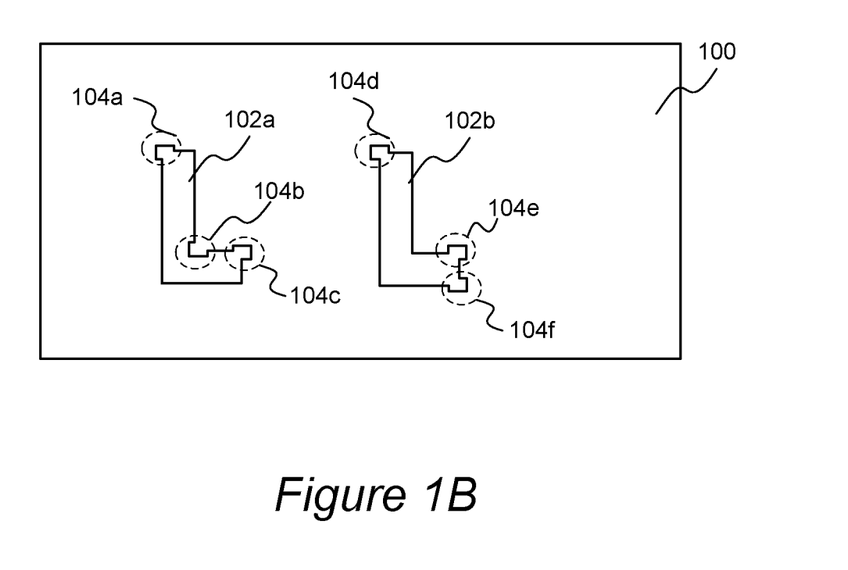
FIG. 1B illustrates the two identical patterns of FIG. 1A with the addition of OPC decorations.

One particular side-effect of OPC software is a high level of inconsistency of the OPC decorations that are placed with respect to identical design patterns. FIG. 1B illustrates the two identical patterns 102a and 102b of FIG. 1A with the addition of different OPC decorations. As shown, the OPC software adds decorations 104a~c to the first L-shaped pattern, while adding OPC decorations 104d~f to identical L-shaped second pattern 102b. In this example, decorations 104a and 104c of pattern 102a have a same shape and location as the decorations 104d and 104e of pattern 102b. In contrast, second pattern 102b has an additional OPC decoration 104f, while the first pattern 102a has a decoration 104b in the form of removed notch portion 104b in the "crook" of the L shape, while L-shaped pattern 102b remains intact in this same area.

The OPC software for adding OPC decorations may be executed on a same pre-OPC layout and result in different OPC decorations for various reasons. For instance, the type and number of OPC decorations for a given feature may depend on the order such particular feature is analyzed with respect to other features. Additionally, an edge feature of a feature array may be given a different OPC decoration than an identical center feature in the same array. OPC software may add different OPC decorations to identical features that have different contextual features or background. Even features having a same context may be given different OPC decorations based on grid snap differences between different features.

Although some inspection processes have worked well for reticles having variable OPC decorations, some inspections of reticles with numerous and variable OPC decorations for identical features will tend to result in an unmanageable set of candidate events. In one example, a single-die inspection includes algorithms for analyzing the image features of a reticle to identify unusual events, which tend to include different OPC decorations for the underlying design features (e.g., pre-OPC features). For instance, the single-die inspection process may define different decorations (104b of pattern 102a, 104f of pattern 102b) as unusual or candidate events. Since the OPC software tends to result in a high number of variable OPC decorations, a high number of candidate events are typically flagged during a single-die inspection of such a reticle pattern.

Additionally, a reticle may include artifacts (e.g., extra or missing material) that were not intended by the designers to be part of the reticle design pattern. However, certain unintentional artifacts may be determined to not limit the yield of wafers produced with such reticle. The single-die inspection may also identify non-printing or non-yield-limiting unusual events as candidate defects.

Certain embodiments of the present invention include filtering from an inspection report defect candidate events, which are found in a current inspection and were also found in a previous inspection on the reticle when it was known to be within specifications. The filtered candidate events and their image data are removed from the system's memory and not analyzed further in a defect review process, for example.

Figure 2:
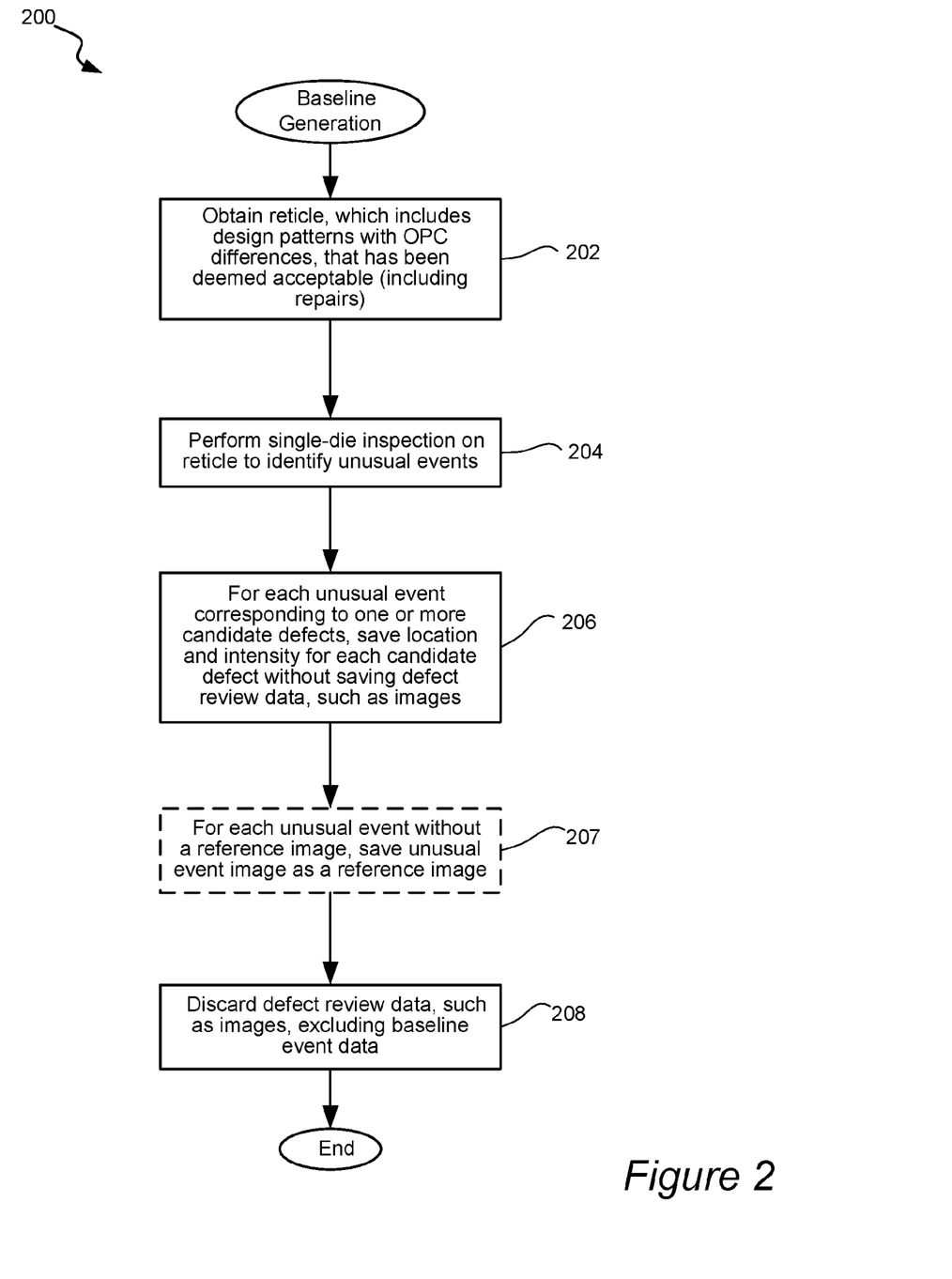
FIG. 2 is a flow chart illustrating a process for generating a baseline of candidate events in accordance with one embodiment of the present invention.

FIG. 2 is a flow chart illustrating a process 200 for generating a baseline of candidate events in accordance with one embodiment of the present invention. Initially, a reticle that has been deemed acceptable may be obtained in operation 202. This reticle has been found to meet a predetermined set of specifications. For instance, a reticle may have been previously inspected using any suitable inspection technique and deemed to not contain any defects that would affect yield or cause a printable error on the wafer. A reticle may be verified or defined as having substantially no degradation or defects by any suitable manner. For example, a buyer of a newly manufactured reticle may assume that the reticle has been verified by the manufacturer as free of defects and degradation. Alternatively, the reticle may be inspected with an optical or scanning electron microscope to determine whether there are any CD uniformity defects on the reticle or the reticle has degraded, for example, by performing a die-to-database inspection. A reticle may be similarly inspected after cleaning to remove haze, as well as other types of degradation and defects.

This known-good reticle includes design patterns that were designed to be identical prior to placement of OPC decorations. That is, the pre-OPC design data contains any number and type of identical patterns. The known-good reticle also includes different OPC decorations formed with respect to at least some identical design patterns. For example, OPC software has added OPC decorations so as to alter the pre-OPC design data to include different OPC decorations on previously identical design patterns so as to generate non-identical OPC-decorated patterns.

The known-good reticle may also contain repairs to the original reticle, and these repairs have been determined to result in a reticle that meets a predetermined set of specifications. For example, extra material that was not intended to be part of the reticle pattern may have been removed. In another example, an area of the reticle that was missing material (e.g., as compared to the intended design pattern) may have been repaired so as to add material to such area.

A single-die inspection may then be performed on the reticle to identify unusual events in operation 204. One type of inspection is a single-die inspection that includes implementing a statistical analysis on the image features of a die to locate unusual events, which each may correspond to one or more "candidate events or defects." A single-die inspection process may include any suitable operations for processing image features to identify candidate events. For instance, any suitable combination of image processing techniques can be used to analyze the image features and determine which features are atypical, given the context of such features. In one simple example, if an array of mostly identical bars includes a single bar with a notch formed on the side, the notch may be deemed a candidate defect.

Some example single-die approaches include template matching and principal component analysis. Template matching is an image processing technique for using common template features as references to locate unusual features. For instance, a first image feature is grabbed and compared or matched to other features. The first image feature is defined as an unusual or candidate event if there is not another feature (or an insignificant number of features) that matches the first image feature. An exhaustive template matching approach can be used to grab and compare each image feature to the other features. Alternatively, other processes can also be implemented to more intelligently and efficiently locate unusual features. For instance, a set of common feature templates can be initially defined before the reticle images are analyzed. The template image features can be transformed into a feature vector for comparison to other feature vectors. Additionally, certain features can be defined as unusual events even if there are multiple similar events. For example, small features that appear in an otherwise 0D or 1D pattern may be identified as unusual events.

For each identified unusual event corresponding to one or more candidate defects, the location and intensity for each candidate defect can be saved without saving defect review data, such as the images, in operation 206. Said in another way, the defect review data, such as images and excluding baseline event data, is discarded in operation 208. The baseline event data may pertain to deliberate unusual events, such as unusual events cause by OPC decoration variation for substantially identical design patterns. That is, at least some of the baseline events will general correspond to reticle features, which were designed to be identical prior to an optical proximity correction process (OPC) being implemented on such reticle features to add OPC decorations so that such reticle features are no longer identical. Such baseline event data may also pertain to unintentional or insignificant events that are deemed to not be real defects or cause yield problems.

The baseline event data contains a minimal set of data for identifying the same events in a subsequent single-die inspection of the reticle at a later time. In the illustrated embodiment, the baseline event data for each candidate defect includes a location, such as x and y coordinates with respect to an origin position on the reticle. An origin position on the reticle may be identified in any suitable manner, such as by one or more origin X and/or Y markings on the reticle. For example, a cross-shaped marking may allow the inspection tool to reference the location of each reticle XY position with respect to the center portion of such marking. Other identifying baseline event data may include an intensity value, as well as on which channel the event data's intensity value was obtained (e.g., transmission or reflecting channel).

One or more candidate defects may be found for each unusual event by first finding a reference for each unusual event. Candidate defects may also be referred to herein as unusual events. Each unique region may be dilated all around by a margin amount. A custom sized rectangular clip or template may then be collected from the original image. This clip contains the original image pixels that correspond to the pixels within the dilated unique region.

A 2D array of weights may be set to be the same size as the rectangular clip. These weights may be used to drive a weighted normalized cross correlation search for a reference region. The weights may be set low where the probability of finding matching pattern is low. The weights can increase as the probability of finding matching pattern increases. Since there is something unique near the centers of the unique clips that make up the unique region, the probability of finding matching pattern near these template centers is low. The probability of finding matching patterns increases with distance from these centers and is highest in the non-unique margins that were added. The weights may be set to follow these trends. The weights may be further adjusted so that edges within the pattern are emphasized over flat areas. The weights for any pixels outside the margins but inside the bounding rectangle may be set to zero.

With the weights set, the reticle image may be searched for a patch of the same size that maximizes the weighted NCC (normalized cross correlation) score. When an on-grid patch produces a peak in the weighted NCC score, interpolation may be used to find the fine alignment that maximizes this score. After searching the reticle image, the aligned patch with the highest score may be selected as the reference. If the best-weighted NCC score fails to exceed a minimum threshold, then no suitable reference is found.

For regions that are primarily 0D or 1D, references can be synthesized, instead of found in the reticle image. If an entire region could have been labeled 0D, except for the weak (and strong) axis gradients near the region's center, a 0D reference can be synthesized. All pixels within the synthetic reference may be set to the mean of the test region's margin pixels. This technique can build a purely 0D reference that best fits the test region's margin pixels. If an entire region could have been labeled 1D except for the weak axis gradients near the unusual test region's centers, a 1D reference can be synthesized. For horizontal patterns, each row of pixels in the synthetic reference can be set to the mean of the test region's margin pixels for that row. For vertical patterns, each column of pixels in the synthetic reference can be set to the mean of the test region's margin pixels for that column. For diagonal patterns, the concept can be the same (e.g., build a purely 1D synthetic reference that best fits the test region's margin pixels).

If no reference is found or synthesizable, the particular "test" or unusual region can be labeled as uninspected and no further processing is done on that region. If a reference is found, the reference clip is collected and compensated. The collection may use interpolation to incorporate the fine alignment offset. The compensation may use a weighted fitting function to compute correction terms. Lighter weights may be used in the uncertain areas of the region so as to relax the fit in those areas. Once the corrections are computed they are applied to the reference clip.

Each unusual event's test image may be compared to a corresponding reference image (if found). If the difference between a particular area of the reference and test images is above a predetermined threshold, such area (e.g., each peak) may be identified as a candidate defect.

For each unusual event for which a reference image cannot be found, the unusual event's image may be stored as a reference image for a subsequent requalification inspection on the same area (operation 207) as further described below. Such an event may be deemed uninspectable.

Figure 3:
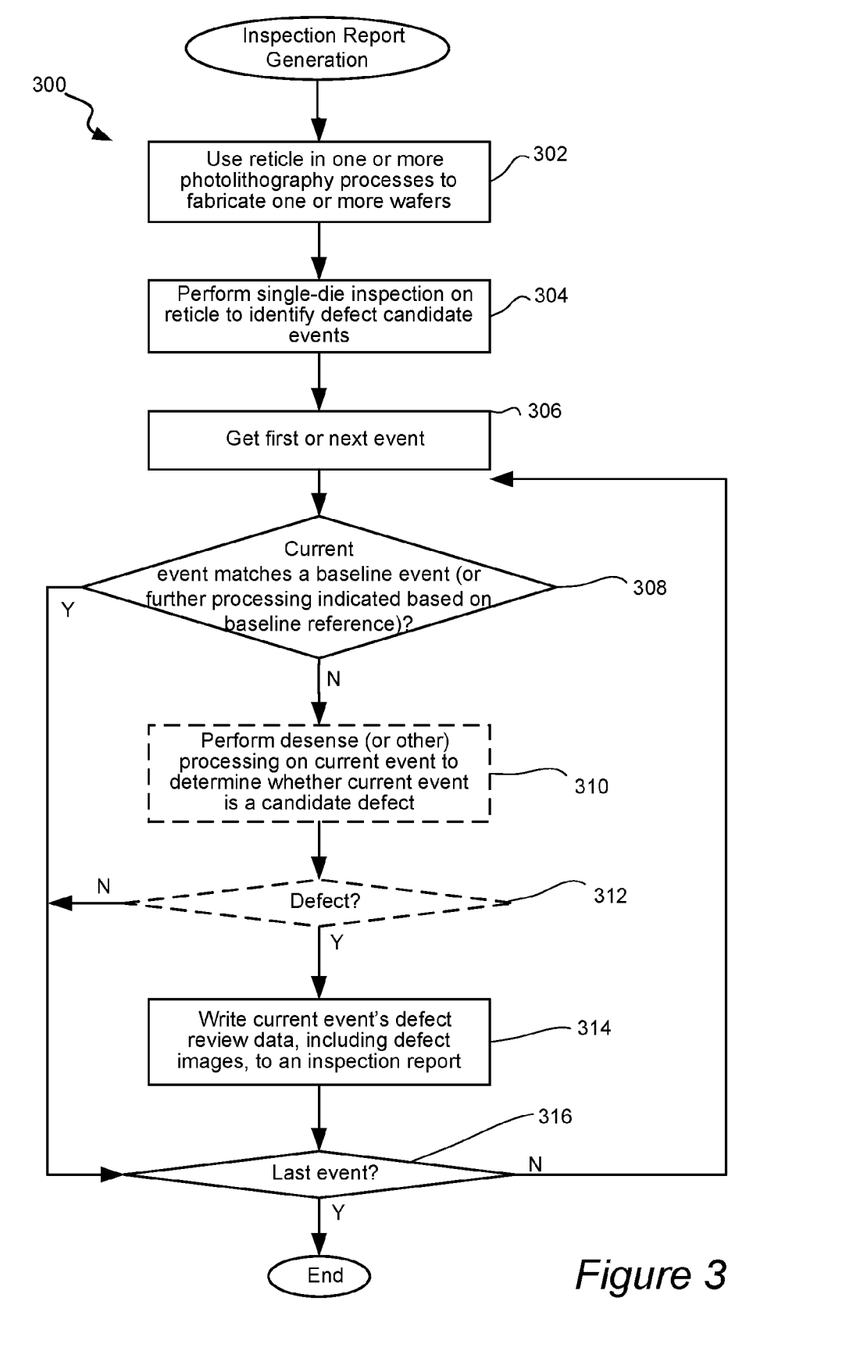
FIG. 3 is a flow chart illustrating an inspection procedure for generating an inspection report in accordance with a specific implementation of the present invention.

The baseline event data may then be used in subsequent requalification inspections of the reticle as further described herein. FIG. 3 is a flow chart illustrating an inspection procedure 300 for generating an inspection report in accordance with a specific implementation of the present invention. The reticle may be used in one or more photolithography processes to fabricate one or more wafers in operation 302.

A single-die inspection may then be performed on the reticle to identify unusual events in operation 304. A single die inspection that is similar to the above-described inspection for the baseline reticle may be performed. However, if a reference image is not found or synthesizable for a particular unusual event, the reference image for the same location in the baseline image and that was previously stored may be obtained and used for finding unusual events that could correspond to candidate defects.

A first event may then be obtained in operation 306, and it may be determined whether this current event matches a baseline event in operation 308. For example, it is determined whether the current event has a substantially similar location and intensity (and possibly channel) as a baseline event. Although this process is described as analyzing events one at a time, this illustrated process is described this way for ease of discussion. The events would more likely be analyzed in parallel as events are identified in images that are being processed in parallel as described further herein.

If an event from the current inspection is determined to not match a baseline event, any suitable type of further defect analysis may be performed. For instance, desense processing may optionally be performed on the current event to determine whether the current event is a candidate defect in operation 310. In general, any process may be used to determine whether a current event is a candidate defect in operation 312. For example, a less stringent (or different) threshold or algorithm, as compared with the threshold or algorithm that was used to identify the event as an unusual event, may be used to determine whether the current event is a candidate defect for particular predefined areas or feature types of the reticle that have been identified as being less sensitive to unusual events/artifacts. That is, a user may have set up a recipe to analyze different types of features (e.g., edges, etc.) in a different manner.

If it is determined that the current event is a candidate defect, the current candidate event's defect review data, including defect images, may be written to an inspection report in operation 314. Alternatively, the current event may simply be written to the inspection report without further defect analysis.

Other post-processing for an unusual event may include preparing the event for saving as a candidate defect entry for an inspection report. For each candidate event that is not matched to a previous baseline event, the inspection report may contain any suitable defect review data. For instance, the defect review data may include both reflective (R) and transmission (T) channel images, a difference image between the R and T images, reference R and T images (generated from the single-die process), thumbnail images, intermediate computations to find candidate events, etc.

In contrast, if a current event does not match a baseline event, further defect analysis may be skipped. Additionally, the current event's review data is not written to the inspection report (i.e., operation 314 is skipped). Since defect review data, including numerous images, are not saved as an entry in an inspection report, the inspection report is not likely to reach data size limits. In some inspections, the data pipeline for all the unusual events prior to filtering such events can be 100 times larger than the defect review data that is eventually saved for the inspection report. Data savings for the inspection report, which excludes events that are similar to baseline events, can be significant.

A baseline event and a current event may be determined to match if their locations are at a same location relative to the reticle origin or within a predetermined distance of each other, such as within 0.5 um distance of each other and the baseline and current events have a similar size if the size values are equal or within a 30% of each other. Otherwise, the current event is deemed a new event and kept for the inspection report.

After the current event is processed, it may then be determined whether this is the last event in operation 316. If this is not the last event, the next event may be obtained and processed. Otherwise, the inspection report generation process ends.

Figure 4:
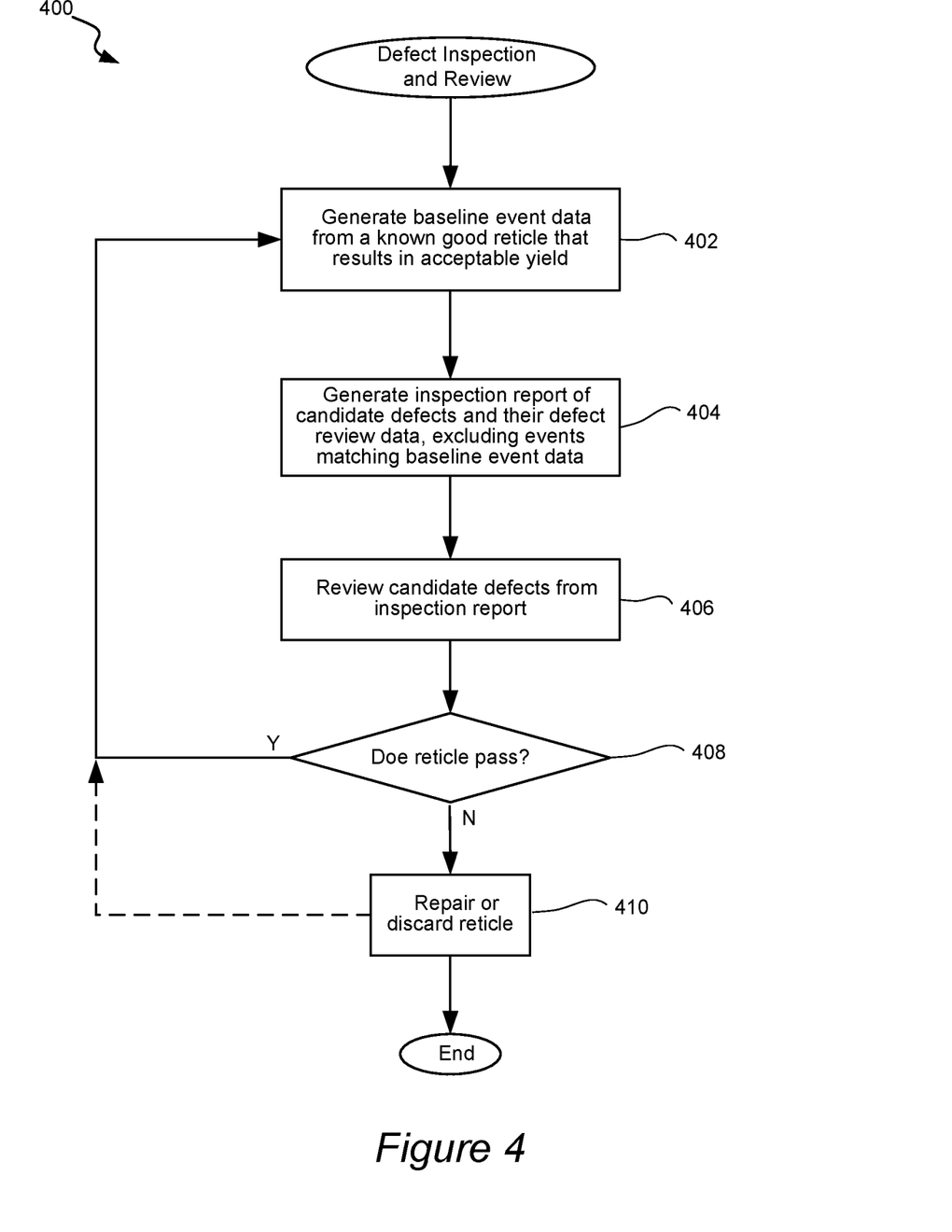
FIG. 4 illustrates an overview of an inspection and defect review procedure in accordance with one embodiment.

FIG. 4 illustrates an overview of an inspection and defect review procedure 400 in accordance with one embodiment. As shown, baseline event data may be generated from a known good reticle, which results in acceptable yield, in operation 402. Baseline event data may be obtained by the baseline events generation procedure of FIG. 1. Images from a known good reticle may be obtained using any suitable inspection tool. Alternatively, images may be simulated based on the design database, including the OPC decorations. For instance, a reticle fabrication process may be simulated with respect to the design data. The reticle images are then analyzed, for example, by a single-die process to generate a baseline events list for the known good reticle.

An inspection report of candidate defects and their associated defect review data, excluding events that substantially match any baseline events, may then be generated in operation 404. For instance, the inspection report generation process of FIG. 2 may be implemented to generate a list of candidate defect events from the current reticle that do not include events that match baseline events from the known good reticle.

The remaining candidate events and their review data from the inspection report may then be reviewed in operation 406. For instance, an operator may review the images of each defect to determine whether each defect corresponds to a significant or real defect, which limits yield. Additionally, the remaining defects may be analyzed by a classifier tool that classifies the defects into classes so that a subset of each class may be efficiently reviewed by an operator, as opposed to reviewing all the candidate defects.

It may then be determined whether the reticle passes inspection based on such map in operation 408. For instance, it may be determined whether the size value of the event is above a predefined threshold. If the size is above the predefined threshold, the corresponding reticle portion may then be more carefully reviewed to determine whether the reticle is defective and can no longer be used.

If the reticle does not pass, the reticle can either be repaired or discarded in operation 410 and inspection ends. If the reticle passes, however, another baseline of events may again be generated for the reticle in operation 402. That is, the reticle may be determined to be within specification, and a new set of baseline events may then be determined for such known good reticle. Likewise, after repair, a baseline event list may also be determined for the repaired reticle.

After the reticle (repaired or passing reticle) is again used, the reticle may again be inspected for new events based on a new or previous baseline of events. In an alternative embodiment for a repaired reticle, the previous baseline of events and a list of repair locations may be used for subsequent inspections of the repaired reticle. That is, if a subsequent inspection results in additional events that do not match the location of the current baseline set or does not correspond to repair location, only these new events may be included in an inspection report for the repaired reticle.

Certain embodiments of the present invention generally provide techniques for communicating unusual events for a known good reticle in a manner that minimizes file size by including a minimum amount of data, e.g., by not including images for such events. For instance, the baseline of events may in some cases only include location and size data (and possibly an indication as to which channel was used) for each detected unusual event of a known good reticle. Since the baseline data tends to be inspection tool independent, the baseline data can be used in subsequent inspections of the reticle on different inspection tools. That is, location and size are stable across different inspection tools.

Images of a single die reticle may be obtained using any inspection tool, such as an optical inspection system, that is set up in any suitable manner. The inspection system is generally set up with a set of operating parameters or a "recipe." Recipe settings may include one or more of the following settings: a setting for scanning the reticle in a particular pattern, pixel size, a setting for grouping adjacent signals from single signals, a focus setting, an illumination or detection aperture setting, an incident beam angle and wavelength setting, a detector setting, a setting for the amount of reflected or transmitted light, aerial modeling parameters, etc. The same or different recipe or the same or different inspection tool may be used to inspect the same reticle for the baseline and one or more subsequent requalification inspections.

In some embodiments, the images of the single die for the different inspections have a same alignment so that the imaged patterns' size and locations from different inspection can be compared to each other. Any suitable approach may be used to align the images to a same coordinate system or origin across inspections. For example, each inspection can align the reticle so that images are obtained relative to a same origin on the reticle. The reticle origin may take the form of one or more reference marks for aligning the reticle.

The inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. A reticle image may be generated after all the positions of the reticle are scanned and converted into detected signals, or potions of a reticle image may be generated as each reticle portion is scanned with the final reticle image being complete after the entire reticle is scanned.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented.

The data for the detected signals for each set of one or more reticle portions or "patches" may be sent to parallel patch processors. For instance, the intensity values for a first patch may be sent to a first processor, and the intensity values for a second patch may be sent to a second processor. Alternatively, the data for a predefined number of patches may be sent to individual patch processors.

Figure 5:
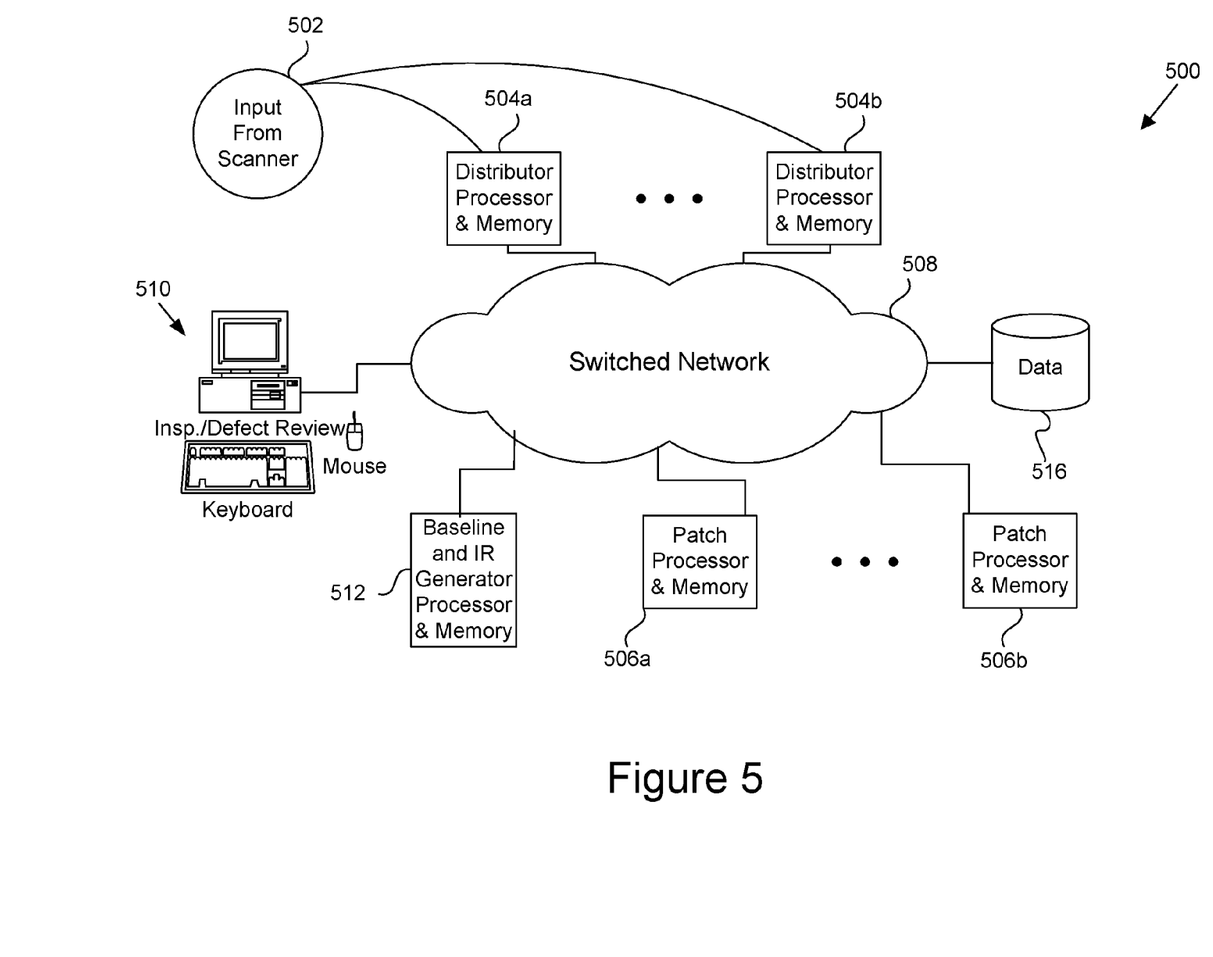
FIG. 5 is a diagrammatic representation of an example inspection system in which techniques of the present invention may be implemented

Techniques of the present invention may be implemented in any suitable combination of hardware and/or software. FIG. 5 is a diagrammatic representation of an example inspection system 500 in which techniques of the present invention may be implemented. The inspection system 500 may receive input 502 from an inspection tool or scanner (not shown). The inspection system may also include a data distribution system (e.g., 504*a* and 504*b*) for distributing the received input 502, an intensity signal (or patch) processing system (e.g., patch processors and memory 506*a* and 506*b*) for processing specific portions/patches of received input 502, a baseline generator system (e.g., Baseline Generator Processor and Memory 512) for generating baseline events, a network (e.g., switched network 508) for allowing communication between the inspection system components, an optional mass storage device 516, and one or more inspection control and/or review stations (e.g., 510) for reviewing the candidate defects. Each processor of the inspection system 500 typically may include one or more microprocessor integrated circuits and may also contain interface and/or memory integrated circuits and may additionally be coupled to one or more shared and/or global memory devices.

The scanner or data acquisition system (not shown) for generating input data 502 may take the form of any suitable instrument (e.g., as described further herein) for obtaining intensity signals or images of a reticle (or other specimen). For example, the scanner may construct an optical image or generate intensity values of a portion of the reticle based on a portion of detected light that is reflected, transmitted, or otherwise directed to one or more light sensors. The scanner may then output the intensity values or image may be output from the scanner.

Intensity or image data 502 can be received by data distribution system via network 508. The data distribution system may be associated with one or more memory devices, such as RAM buffers, for holding at least a portion of the received data 502. Preferably, the total memory is large enough to hold at least an entire swath of data. For example, one gigabyte of memory works well for a reticle swath of patches that is 1 million by 1000 pixels or points.

The data distribution system (e.g., 504*a* and 504*b*) may also control distribution of portions of the received input data 502 to the processors (e.g. 506*a* and 506*b*). For example, data distribution system may route data for a first patch to a first patch processor 506*a*, and may route data for a second patch to patch processor 506*b*. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well for intensity values or an image corresponding to a patch that is 512 by 1024 pixels. Alternatively, the patch processors may share memory.

Each set of input data 502 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 506a, and the second memory partition may hold and route second data to patch processor 506b.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

Figure 6A:
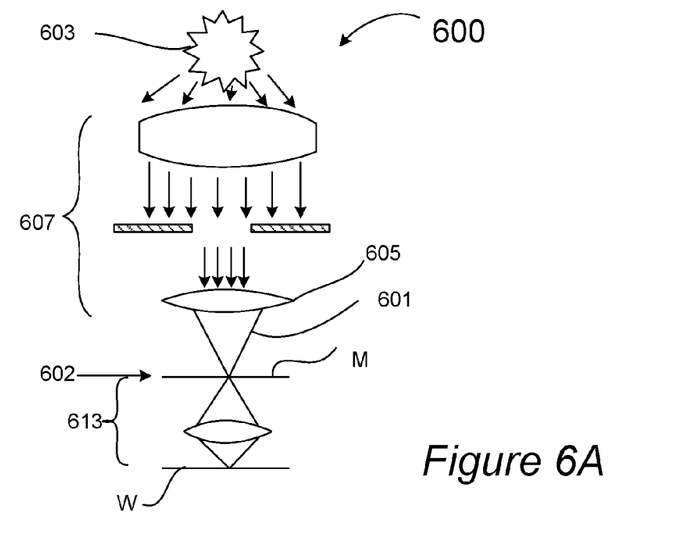
FIG. 6A is a simplified schematic representation of a lithographic system for transferring a mask pattern from a photomask onto a wafer in accordance with certain embodiments.

FIG. 6A is a simplified schematic representation of a typical lithographic system 600 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 603 directs a light beam through an illumination optics 607 (e.g., lens 605) onto a photomask M located in a mask plane 602. The illumination lens 605 has a numeric aperture 601 at that plane 602. The value of the numerical aperture 601 impacts which defects on the photomask are lithographic significant defects and which ones are not. A portion of the beam that passes through the photomask M forms a patterned optical signal that is directed through imaging optics 613 and onto a wafer W to initiate the pattern transfer.

Figure 6B:
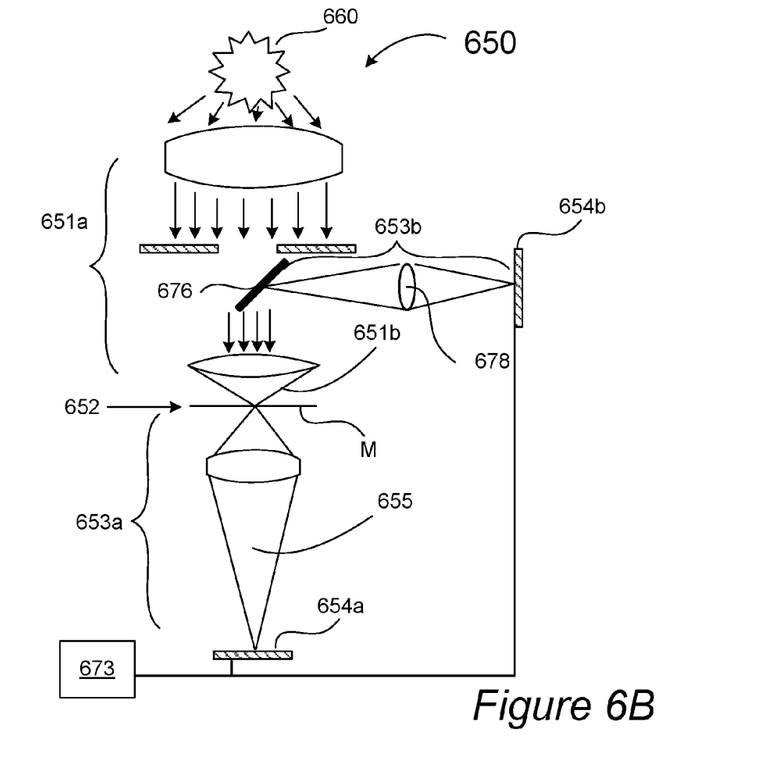
FIG. 6B provides a schematic representation of a photomask inspection apparatus in accordance with certain embodiments.

FIG. 6B provides a schematic representation of an example inspection system 650 that has illumination optics 651a includes an imaging lens with a relative large numerical aperture 651b at a reticle plane 652 in accordance with certain embodiments. The depicted inspection system 650 includes detection optics 653a and 653b, including microscopic magnification optics designed to provide, for example, 60-200× magnification or more for enhanced inspection. For example, the numerical aperture 651b at the reticle plane 652 of the inspection system may be considerable greater than the numerical aperture 601 at the reticle plane 602 of the lithography system 600, which would result in differences between test inspection images and actual printed images.

The inspection techniques described herein may be implemented on various specially configured inspection systems, such as the one schematically illustrated in FIG. 6B. The illustrated system 650 includes an illumination source 660 producing a light beam that is directed through illumination optics 651a onto a photomask M in the reticle plane 652. As explained above, the inspection system 650 may have a numerical aperture 651b at the reticle plane 652 that may be greater than a reticle plane numerical aperture (e.g., element 601 in FIG. 6A) of the corresponding lithography system. The photomask M to be inspected is placed on a mask stage at the reticle plane 652 and exposed to the source.

The patterned image from the mask M is directed through a collection of optical elements 653a, which project the patterned image onto a sensor 654a. In a reflecting system, optical elements (e.g., beam splitter 676 and detection lens 678) direct and capture the reflected light onto sensor 654b. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 654a and/or 654b) can be processed by a computer system 673 or, more generally, by one or more signal processing devices, which may each include an analog-to-digital converter configured to convert analog signals from each sensor into digital signals for processing. The computer system 673 typically has one or more processors coupled to input/output ports, and one or more memories via appropriate buses or other communication mechanisms.

The computer system 673 may also include one or more input devices (e.g., a keyboard, mouse, joystick) for providing user input, such as changing focus and other inspection recipe parameters. The computer system 673 may also be connected to the stage for controlling, for example, a sample position (e.g., focusing and scanning) and connected to other inspection system components for controlling other inspection parameters and configurations of such inspection system components.

The computer system 673 may be configured (e.g., with programming instructions) to provide a user interface (e.g., a computer screen) for displaying resultant intensity values, images, and other inspection results. The computer system 673 may be configured to analyze intensity, phase, and/or other characteristics of reflected and/or transmitted sensed light beam. The computer system 673 may be configured (e.g., with programming instructions) to provide a user interface (e.g., on a computer screen) for displaying resultant intensity values, images, and other inspection characteristics. In certain embodiments, the computer system 673 is configured to carry out inspection techniques detailed above Because such information and program instructions may be implemented on a specially configured computer system, such a system includes program instructions/computer code for performing various operations described herein that can be stored on a non-transitory computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a photolithographic reticle, the method comprising:
    performing a first inspection of a reticle that has been identified as being within specifications so as to generate a plurality of baseline candidate defects and their location and size;
    after using the reticle in one or more photolithography processes after the first inspection, performing via a reticle inspection tool a second inspection of the reticle so as to generate a plurality of current candidate defects and their location and size values; and
    generating an inspection report of a plurality of filtered candidate defects and their images, wherein the filtered candidate defects include a first subset of the current candidate defects and their corresponding plurality of candidate defect images and exclude a second subset of the current candidate defects and their corresponding plurality of excluded images, wherein each of the first subset of current candidate defects included in the inspection report has a location and size value that fails to match any baseline candidate defect's location and size value by a predefined amount, and each of the second subset of current candidate defects excluded from the inspection report has a location and size value that matches any baseline candidate defect's location and size value by the predefined amount.

2. The method of claim 1, wherein at least some of the baseline candidate defects correspond to a plurality of reticle features that were designed to be identical prior to an optical proximity correction (OPC) process being implemented on such reticle features to add OPC decorations so that such reticle features are no longer identical.

3. The method of claim 1, wherein at least some of the baseline candidate defects correspond to reticle features that were not part of an original design for such reticle and were determined to not limit wafer yield using such reticle.

4. The method of claim 1, wherein at least some of the baseline candidate defects correspond to reticle features that have been determined to not print onto a wafer during a photolithography process using the reticle.

5. The method of claim 1, wherein at least some of the baseline candidate defects correspond to repair features for correcting defects on the reticle.

6. The method of claim 1, wherein the first and second inspections determine which features of the reticle are atypical and correspond to baseline candidate defects and current candidate defects, respectively, based on the context of such features, and wherein the first and second inspections include template matching.

7. The method of claim 1, further comprising discarding a plurality of baseline images for the baseline candidate defects and discarding the second subset of current candidate defects' corresponding images.

8. The method of claim 1, wherein each baseline candidate defect further indicates a channel and each of the second subset of current candidate defects excluded from the inspection report has a channel and a location and size value that matches any baseline candidate defect's channel and location and size value by a predefined amount.

9. The method of claim 1, wherein generating the inspection report of the filtered candidate defects and their images comprises:
    for each current candidate defect that has a location and size value that fails to match any baseline candidate defect's location and size value by a predefined amount, determining whether such current candidate defect remains a current candidate defect by performing a third inspection that has a less stringent threshold or algorithm than the second inspection.

10. The method of claim 1, wherein the filtered candidate defects further include a third subset of current candidate defects that each has a location and size value that matches any baseline candidate defect's location and size value by a predefined amount and is identified as a repair location.

11. The method of claim 1, wherein the first inspection is performed using a reticle inspection tool.

12. The method of claim 1, wherein the first inspection is performed on a reticle image that was generated from design database.

13. The method of claim 1, wherein the reticle is an EUV reticle.

14. The method of claim 1, wherein the current candidate defects include a particle on the reticle.

15. An inspection system for inspecting a photolithographic reticle, the system comprising at least one memory and at least one processor that are configured to perform the following operations:
    for a reticle, obtaining a plurality of baseline candidate defects and their location and size that were generated from a first inspection that has been identified as being within specifications;
    after using the reticle in one or more photolithography processes after the first inspection, performing via a reticle inspection tool a second inspection of the reticle so as to generate a plurality of current candidate defects and their location and size values; and
    generating an inspection report of a plurality of filtered candidate defects and their images, wherein the filtered candidate defects include a first subset of the current candidate defects and their corresponding plurality of candidate defect images and exclude a second subset of the current candidate defects and their corresponding plurality of excluded images, wherein each of the first subset of current candidate defects included in the inspection report has a location and size value that fails to match any baseline candidate defect's location and size value by a predefined amount, and each of the second subset of current candidate defects excluded from the inspection report has a location and size value that matches any baseline candidate defect's location and size value by the predefined amount.

16. The system of claim 15, wherein at least some of the baseline candidate defects correspond to a plurality of reticle features that were designed to be identical prior to an optical proximity correction (OPC) process being implemented on such reticle features to add OPC decorations so that such reticle features are no longer identical.

17. The system of claim 15, wherein at least some of the baseline candidate defects correspond to reticle features that were not part of an original design for such reticle and were determined to not limit wafer yield using such reticle.

18. The system of claim 15, wherein at least some of the baseline candidate defects correspond to reticle features that have been determined to not print onto a wafer during a photolithography process using the reticle.

19. The system of claim 15, wherein at least some of the baseline candidate defects correspond to repair features for correcting defects on the reticle.

20. The system of claim 15, wherein the first and second inspections determine which features of the reticle are atypical and correspond to baseline candidate defects and current candidate defects, respectively, based on the context of such features, and wherein the first and second inspections include template matching.

21. The system of claim 15, wherein the at least one memory and at least one processor are further configured for discarding a plurality of baseline images for the baseline candidate defects and discarding the second subset of current candidate defects' corresponding images.

22. The system of claim 15, wherein each baseline candidate defect further indicates a channel and each of the second subset of current candidate defects excluded from the inspection report has a channel and a location and size value that matches any baseline candidate defect's channel and location and size value by a predefined amount.

23. The system of claim 15, wherein generating the inspection report of the filtered candidate defects and their images comprises:

for each current candidate defect that has a location and size value that fails to match any baseline candidate defect's location and size value by a predefined amount, determining whether such current candidate defect remains a current candidate defect by performing a third inspection that has a less stringent threshold or algorithm than the second inspection.

24. The system of claim 15, wherein the filtered candidate defects further include a third subset of current candidate defects that each has a location and size value that matches any baseline candidate defect's location and size value by a predefined amount and is identified as a repair location.

25. The system of claim 15, wherein the first inspection is performed using the inspection system.

26. The system of claim 15, wherein the first inspection is performed on an reticle image that was generated from design database.

27. The system of claim 15, wherein the reticle is an EUV reticle.

28. The system of claim 15, wherein the current candidate defects include a particle on the reticle.

\* \* \* \* \*